(12) United States Patent  
Marumori et al.

(10) Patent No.: US 9,050,155 B2
(45) Date of Patent: Jun. 9, 2015

(54) IMPRESSION TRAY FOR UPPER JAW

(71) Applicant: GC CORPORATION, Tokyo (JP)

(72) Inventors: Hidefumi Marumori, Yokohama (JP); Hiroshi Kamohara, Matsudo (JP)

(73) Assignee: GC CORPORATION, Tokyo (JP)

( * ) Notice: Subject to any disclaimer, the term of this patent is extended or adjusted under 35 U.S.C. 154(b) by 24 days.

(21) Appl. No.: 13/853,482

(22) Filed: Mar. 29, 2013

(65) Prior Publication Data

US 2013/0260331 A1    Oct. 3, 2013

(30) Foreign Application Priority Data

Mar. 30, 2012  (JP) ................................. 2012-080341

(51) Int. Cl.
*A61C 9/00*         (2006.01)
(52) U.S. Cl.
CPC .................................... *A61C 9/0006* (2013.01)
(58) Field of Classification Search
CPC ................................................... A61C 9/0006
USPC .............................. 433/34, 36, 37, 35, 41–48
See application file for complete search history.

(56) References Cited

U.S. PATENT DOCUMENTS

| | | | |
|---|---|---|---|
| 4,445,854 A * | 5/1984 | Bekey et al. ..................... | 433/37 |
| 5,076,785 A * | 12/1991 | Tsai ................................ | 433/46 |
| 5,336,086 A * | 8/1994 | Simmen et al. ................. | 433/37 |
| 5,752,826 A | 5/1998 | Andreiko | |
| 2005/0106529 A1 | 5/2005 | Abolfathi et al. | |

FOREIGN PATENT DOCUMENTS

JP          2000-135227        5/2000
WO     WO 2007/142474 A2    12/2007

OTHER PUBLICATIONS

Extended Search Report issued Jun. 28, 2013 in European Patent Application No. 13001612.4.
U.S. Appl. No. 13/853,420, filed Mar. 29, 2013, Marumori et al.
U.S. Appl. No. 13/782,397, filed Mar. 1, 2013, Marumori et al.
U.S. Appl. No. 29/425,723, filed Jun. 26, 2012, Marumori et al.
U.S. Appl. No. 29/425,716, filed Jun. 26, 2013, Marumori et al.
U.S. Appl. No. 29/425,712, filed Jun. 26, 2012, Marumori et al.

* cited by examiner

*Primary Examiner* — Ralph Lewis
(74) *Attorney, Agent, or Firm* — Oblon, McClelland, Maier & Neustadt, L.L.P.

(57) ABSTRACT

The invention provides a plastic impression tray for an upper jaw having a bottom portion provided with an outer wall and a bulge portion. A rim is provided along an upper end of the outer wall, elongated through holes having a particular width are provided in the outer wall such that a distance between the adjacent through holes is particular times the width, similar elongated through holes are provided in the bulge portion, circular through holes having a particular diameter are provided at the center of the distances of the adjacent elongated through holes in the outer wall, and elongated end portion side through holes having particular width and length are provided on a line connecting the bottom portion side end portions of the elongated through holes at the closest side to the end portions of the U-like shaped portion in the outer wall and the bulge portion.

6 Claims, 3 Drawing Sheets

IMPRESSION TRAY FOR UPPER JAW

CROSS REFERENCE TO RELATED APPLICATION

This application claims priority to Japanese Patent Application No. 2012-080341, filed Mar. 30, 2012, the text of which is incorporated herein by reference.

BACKGROUND OF THE INVENTION

1. Field of the Invention

The present invention relates to a plastic impression tray for an upper jaw to be used for taking an impression of an upper jaw within an oral cavity as a preparation stage of producing a complete denture as a prosthetic appliance in dentistry, wherein the impression tray for an upper jaw can prevent a set impression material from floating upward from the tray and being peeled off from the tray, and therefore can take impression with high accuracy.

2. Description of the Conventional Art

In a dental care, an impression material such as a silicone impression material or an alginate impression material is used for taking an impression within an oral cavity as a preparation stage of producing a prosthetic appliance. For inserting and retaining such an impression material within the oral cavity, an impression tray is used. In the impression taking, the impression material is loaded in the impression tray so as to be inserted into the oral cavity of a patient, the impression material is pressed into the oral cavity of the patient to be carried out the impression taking, the impression material is set, and the impression material is thereafter taken out of the oral cavity of the patient integrally in a state in which the set impression material is retained in the impression tray.

Large force is necessary at a time of taking out the set impression material from the oral cavity. As a result, there is a problem that the set impression material floats upward from the impression tray and is peeled off from the impression tray, so that an air gap is generated between the impression tray and the impression material. In the case that the air gap is generated, it is often the case that the impression material deforms from the initial set state, and a precision of the prepared dental prosthetic appliance is significantly lowered. Further, since the impression material has a property that the impression material is shrinked by a reaction and a volatilization of a water content after being set, the impression material is greatly affected by the shrinkage in the case that the impression material is peeled off from the impression tray, whereby a precision of the dental prosthetic appliance is further lowered. Accordingly, for the impression tray, there becomes important a performance that the impression material inserted into the oral cavity of the patient so as to be set can be taken out from the oral cavity of the patient without being deformed.

Generally, the impression tray is provided with a retention hole or a groove for mechanically retaining the set impression material. In other words, the impression material paste before being set enters into the retention hole and is set, whereby the set impression material and the tray are mechanically engaged. Particularly, since the set impression material tends to be peeled off in a peripheral portion of the tray, an application of forming an undercut portion (a rib) along the peripheral portion of the tray is carried out. However, since a sufficient amount of impression material cannot enter into the undercut portion, the peeling tends to be generated in the peripheral portion. Further, the impression tray is made of a metal or a plastic, and the metal tray can be easily formed an undercut having a height of 1.5 to 2.5 mm in the peripheral portion by processing as mentioned above. On the other hand, since the plastic tray is affected by a metal mold which is used for producing the tray and the molded tray cannot be taken out, the plastic tray cannot be formed an undercut having an effective height. Therefore, particularly in the impression tray made of a plastic, a problem that the peeling from the tray peripheral portion of the tray is large and the deformation becomes larger occurs.

As the plastic tray for an upper jaw, there is a dental impression tray which is provided with a bottom wall, and inner and outer walls for forming an impression material retaining concave portion which is similar to a tooth row shape and is formed as a curved shape in a plan view, is provided with a handle portion which extends forward from side ends of front teeth in the bottom wall or the outer wall, and is provided at least in the inner and outer walls of the concave portion with a lot of impression material retention holes which inhibit a relative movement to the impression material over a whole surface (refer, for example, to FIGS. 7 to 10 of Japanese Unexamined Patent Publication No. 2000-135227; hereinafter referred to as Patent Document 1). Patent Document 1 exemplifies a structure in which impression material retention holes provided in inner and outer opposed walls are elongated holes which are elongated shaped in a vertical direction and penetrate in an inward and outward direction of the concave portion (refer to claim 2), and the impression material retention hole provided in a front teeth side of the outer wall is provided in the bottom wall of the concave portion or the handle portion, or both of them and is communicated in a penetrating manner (refer to claim 3). However, Patent Document 1 shows only the structure in which a distance between the adjacent elongated holes in the drawing is very short in the impression material retention holes which are provided in the inner and outer opposed walls and elongated in the vertical direction as mentioned above, and any disclosure of a width of the elongated hole does not exist in Patent Document 1. Further, an impression material retention hole provided in the front teeth side of the outer wall is disclosed as the elongated hole in the drawing, however, a distance between the adjacent elongated holes and a width of the elongated hole does not disclosed. Further, the impression material retention hole having a circular cross sectional shape is provided in the bottom wall, however, a hole diameter and a distance between the adjacent impression material retention holes having the circular cross section shape are not disclosed at all. Further, the bottom wall is shown as an aspect that a U-like shaped end portion side (a back tooth side) becomes rapidly shallow.

In the dental impression tray described in Patent Document 1 mentioned above, it is not assured that the impression material can be sufficiently retained by the impression material retention holes constructed by the elongated holes which are provided in the inner and outer opposed walls and are elongated shaped in the vertical direction, it is not assured that the impression material can be sufficiently retained by the impression material retention hole which is provided in the front teeth side of the outer wall, and it is not assured that the impression material can be sufficiently retained by the impression material retention hole which is provided in the bottom wall and has the circular cross sectional shape. Further, there is a defect that the impression material in the end portion side (the back tooth side) of the U-like shaped form tends to be peeled off.

SUMMARY OF THE INVENTION

Problem to be Solved by the Invention

An object of the present invention is to provide a plastic impression tray for an upper jaw to be used for taking an impression of an upper jaw within an oral cavity as a preparation stage of producing a complete denture as a prosthetic appliance in dentistry, wherein the impression tray can prevent a set impression material from floating upward from the tray and being peeled off from the tray, and therefore can take an impression with a high precision.

Means for Solving the Problem

The inventors of the present invention have devoted themselves to make a study for solving the problem mentioned above. As a result, the inventors have inquired into a fact that the problem mentioned above can be solved by forming a whole shape of the plastic impression tray for an upper jaw as a shape having an outer wall which is provided upright from an outer side of a bottom portion including U-like shaped end portions forming a U-like shaped approximately flat surface with an approximately uniform width via a circular arc shaped portion and is reduced its height gradually toward the end portion side of the U-like shaped portion, and having a bulge portion which bulges from an inner side of the bottom portion so as to form a smooth curved surface and occludes the inner side space between the U-like shaped bottom portions, setting a rim having a height of 0.01 to 1 mm in the bottom portion side along an upper end of the outer wall, forming elongated through holes each of which reaches the bottom portion from a portion just below the rim vertically to the rim and has a width of 1.5 to 4.0 mm in the outer wall which does not include the end portion of the U-like shaped portion in such a manner that a distance between the adjacent through holes is from 2 to 5 times the width of the through hole and is approximately uniform, setting elongated through holes each of which reaches the bottom portion and has the same width as the width of the elongated through hole provided in the outer wall in a section corresponding to the elongated through hole which is provided in the outer wall at a position except a front teeth portion side in the bulge portion and in a section positioned at the center of the front teeth portion side at a position in the front teeth portion side, setting circular through holes each having a diameter of 3 to 6 mm at the center of distances of the adjacent elongated through holes which are provided in the outer wall, and setting an elongated end portion side through holes each of which has a width of 1.0 to 3.0 mm and a length of 5 to 15 mm, on a line which connects the bottom portion side end portions of the respective elongated through holes positioned in the closest side to the end portions of the U-like shaped portion in the outer wall and the bulge portion in the end portions of the U-like shaped portion, or sides which are closer to the end portions than the line and the end portion side in the center of the bulge portion, and the inventors have completed the present invention.

In the structure mentioned above, the inventors have inquired into a fact that it is preferable that the width of the elongated through holes which are provided in the outer wall and the bulge portion is from 2.0 to 3.0 mm, the length is from 2 to 3 times the width, the distance between the elongated through holes which are provided in the outer wall and the bulge portion is from 3 to 18 mm, the height of the rim is from 1 to 0.3 mm, and a rim having a height of 0.01 to 1 mm is provided in an opposite side to the bottom portion along each of the upper ends of the outer wall.

In other words, according to the present invention, there is provided a plastic impression tray for an upper jaw, the impression tray formed as a shape having an outer wall which is provided upright from an outer side of a bottom portion including U-like shaped end portions forming a U-like shaped approximately flat surface with an approximately uniform width via a circular arc shaped portion and is reduced its height gradually toward the end portion side of the U-like shaped portion, and a bulge portion which bulges from an inner side of the bottom portion so as to form a smooth curved surface and occludes the inner side space between the U-like shaped bottom portions, wherein a rim having a height of 0.01 to 1 mm is provided in the bottom portion side along an upper end of the outer wall, elongated through holes each of which reaches the bottom portion from a portion just below the rim vertically to the rim and has a width of 1.5 to 4.0 mm are formed in the outer wall which does not include the end portion of the U-like shaped portion in such a manner that a distance between the adjacent through holes is from 2 to 5 times the width of the through hole and is approximately uniform, elongated through holes each of which reaches the bottom portion and has the same width as the width of the elongated through hole provided in the outer wall are provided in a section corresponding to the elongated through hole which is provided in the outer wall at a position except a front teeth portion side in the bulge portion and in a section positioned at the center of the front teeth portion side at a position in the front teeth portion side, circular through holes each having a diameter of 3 to 6 mm are formed at the center of the distances of the adjacent elongated through holes which are provided in the outer wall in the bottom portion, and elongated end portion side through holes each of which has a width of 1.0 to 3.0 mm and a length of 5 to 15 mm are provided on a line which connects the bottom portion side end portions of the respective elongated through holes positioned in the closest side to the end portions of the U-like shaped portion in the outer wall and the bulge portion in the end portions of the U-like shaped portion, or sides which are closer to the end portions than the line and the end portion side in the center of the bulge portion. In the impression tray for an upper jaw, it is preferable that the width of the elongated through holes is from 2.0 to 3.0 mm, the length is from 2 to 3 times the width, the distance of the long through holes is from 3 to 18 mm, the height of the rim is from 1 to 0.3 mm, and a rim having a height from 0.01 to 1 mm is provided in an opposite side to the bottom portion along each of the upper ends of the outer wall and the inner wall.

Effect of the Invention

Since the impression tray for an upper jaw according to the present invention is provided with the rims having the height of 0.01 to 1 mm, preferably from 0.1 to 0.3 mm, in the bottom portion side along each of the upper ends of the outer wall which is provided from the outer side of the U-like shaped bottom portion, the portion below the rim comes to an undercut portion, so that the set impression material is hard to float upward and be peeled off from the tray. Further, since the height of the rim is from 0.01 to 1 mm and is low, the rim does not form an obstacle to unloading from a metal mold at a time of an injection molding. Further, since the elongated through holes each of which reaches the bottom portion from the portion just below the rim vertically to the rims, has the width of 1.5 to 4.0 mm are formed in the outer wall which does not include the end portions of the U-like shaped portion in such a manner that the distance between the adjacent through holes is from 2 to 5 times the width of the through hole and is approximately uniform, and the through holes each of which reaches the bottom portion, has the same width as the width of the elongated hole provided in the outer wall are provided in a section corresponding to the elongated through hole which is provided in the outer wall at a position except a front teeth portion side in the bulge portion and in a section positioned at the center of the front teeth portion side at a position in the front teeth portion side, the impression material appropriately enters into the through holes at a time of loading the silicone impression material or the alginate impression material within the tray so as to press to the upper jaw within the oral cavity of the patient, thereby taking the impression, and retains the set impression material. Therefore, the set impression material is hard to float upward and be peeled off from the tray. Further, since the circular through holes each having the diameter of 3 to 6 mm are formed in the bottom portion at the center of the distances of the adjacent elongated through holes which are provided in the outer wall, the impression material enters into the circular through holes so as to retain the set impression material at a time of loading the silicone impression material or the alginate impression material within the tray so as to press to the upper jaw within the oral cavity of the patient, thereby taking the impression. However, since the circular through holes do not exist on the line connecting the elongated through holes which are provided in the outer wall and the bulge portion, the impression material loaded on the same portion within the tray is not simultaneously pushed out to an outer side of the tray from the elongated through holes which are provided in the outer wall and the bulge portion and the circular through holes which are provided in the bottom portion, and any space is not generated in the set impression material. Further, since the elongated end portion side through holes which have the width of 1.0 to 3.0 mm and the length of 5 to 15 mm are provided on the line connecting the bottom portion side end portions of the through holes which are positioned in the closest side to the end portion of the U-like shaped portion in the outer wall and the bulge portion in the end portions of the U-like shaped portion, or in the end portion side in the center of the bulge portion in addition to the sides which are closer to the end portions than the line, the impression material loaded on the closest side to the back tooth within the tray enters into the elongated end portion side through holes which are provided in the end portion side in the center of the bottom portion and the bulge portion in the end portions of the U-like shaped portion so as to be firmly retained. Therefore, there is not generated the defect that the impression material in the end portion side (the back teeth side) of the U-like shaped portion tends to be peeled off.

Further, in the impression tray for an upper jaw mentioned above, in the case that the width of the elongated through holes which are provided in the outer wall and the bulge portion is from 2.0 to 3.0 mm, the length thereof is from 2 to 3 times the width, and the distance of the elongated through holes which are provided in the outer wall and the bulge portion is from 3 to 18 mm, the impression material is better retained by the elongated through holes at a time of impression taking, and the set impression material is hard to float upward and be peeled off from the tray. Further, in the case that the rim having the height of 0.01 to 1 mm is provided in the opposite side to the bottom portion along the upper end of the outer wall, a thickness of the upper end of the outer wall is increased and a strength thereof is improved. However, the increase of the thickness does not form an obstacle to unloading from the metal mold at a time of the injection molding.

DETAILED DESCRIPTION OF PREFERRED EMBODIMENT

Figure 1:
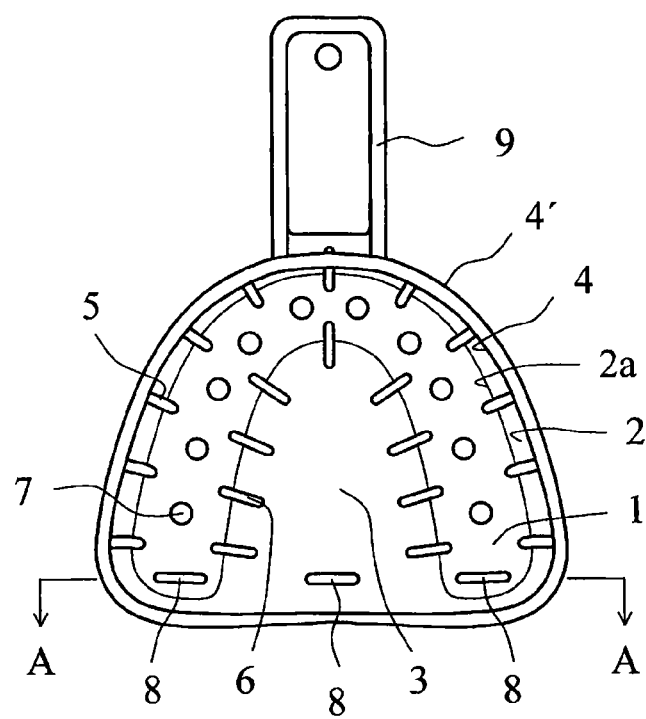
FIG. 1 is a plan view of an embodiment of an impression tray for an upper jaw according to the present invention.
Figure 2:
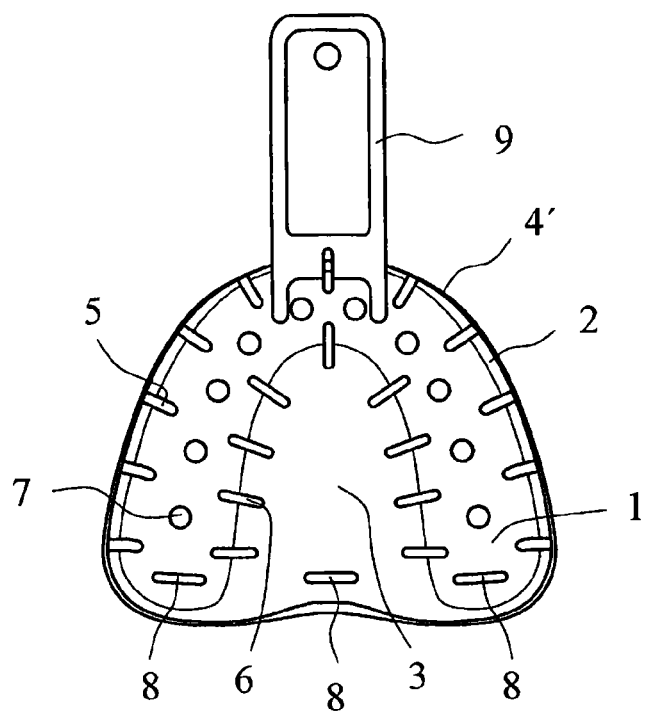
FIG. 2 is a back elevational view of the impression tray for an upper jaw shown in FIG. 1.
Figure 3:
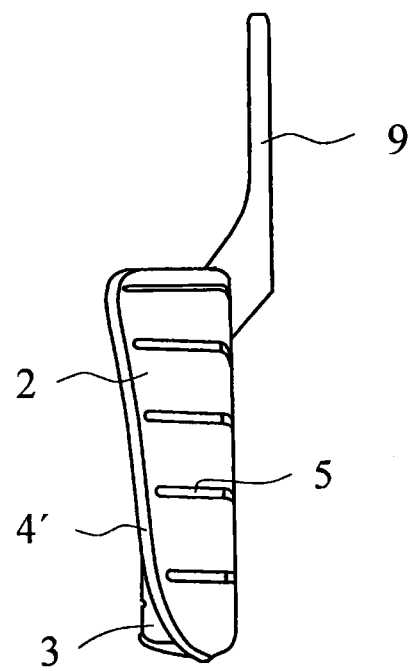
FIG. 3 is a right side elevational view of the impression tray for an upper jaw shown in FIG. 1.
Figure 4:
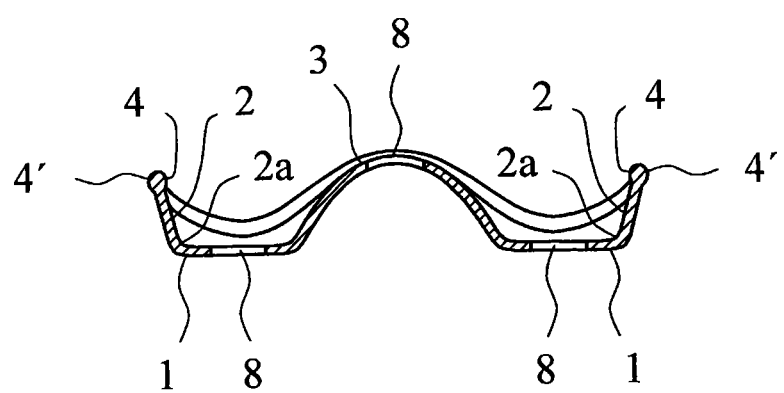
FIG. 4 is an enlarged end elevational view along a line A-A in FIG. 1.
Figure 5:
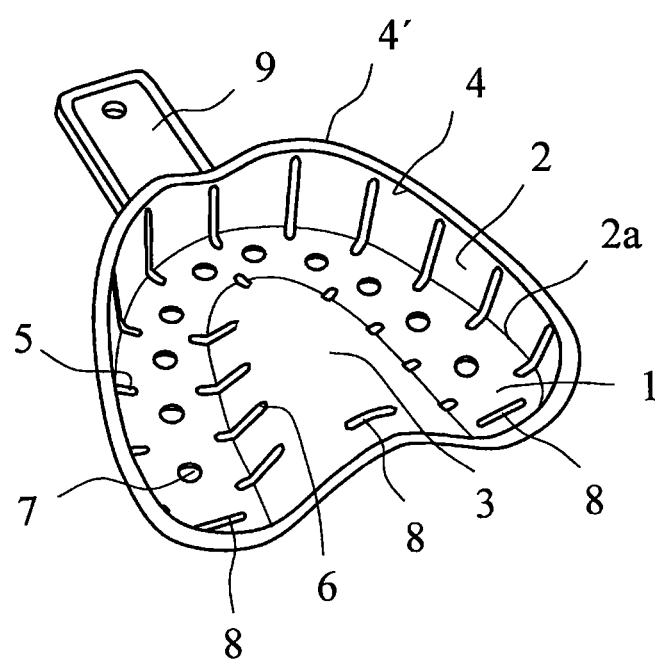
FIG. 5 is a perspective view of the impression tray for an upper jaw shown in FIG. 1.

An impression tray for an upper jaw according to the present invention is a plastic impression tray for an upper jaw, the impression tray being formed so as to have a bottom portion 1 which is formed as a U-like shaped approximately flat surface with an approximately uniform width, an outer wall 2 which is provided upright from an outer side of the bottom portion 1 including U-like shaped end portions via a circular arc shaped portion 2a and is reduced its height gradually toward the end portion side of the U-like shaped portion, and a bulge portion 3 which bulges from an inner side of the bottom portion 1 so as to form a smooth curved surface and occludes the inner side space between the U-like shaped bottom portions 1. Further, a rim 4 having a height of 0.01 to 1 mm, preferably from 0.1 to 0.3 mm is provided in a side of the bottom portion 1 along each of upper ends of the outer wall 2. The rim 4 is provided for forming an undercut portion below the rim 4 so as to generate an effect of preventing a set impression material from floating upward and being peeled off from the tray. If the height of the rim 4 is less than 0.01 mm, an effect of forming the undercut portion cannot be expected, and if the height goes beyond 1 mm, the rim forms an obstacle to unloading from a metal mold at a time of injection molding of the tray due to its excessive height and it is impossible to well carry out the injection molding. Further, in the case that a rim 4' having a height of 0.01 to 1 mm is further provided in an opposite side to the bottom portion 1 along each of the upper ends of the outer wall 2, a thickness of the upper end of the outer wall 2 is increased and a strength thereof is improved. However, the rim 4' does not form an obstacle to unloading from the metal mold at a time of the injection molding and is preferably provided.

Reference numeral 5 denotes a elongated hole which is provided vertically to the rim 4 in the outer wall 2 including no U-like shaped end portion, and has a width of 1.5 to 4.0 mm reaching the bottom portion 1 from a portion just below the rim 4. The through hole 5 is formed such that a distance between the adjacent through holes 5 is approximately equal to 2 to 5 times the width of the through hole 5. If the width of the elongated through hole 5 is less than 1.5 mm, the impression material does not appropriately enter into the through holes 5 at a time of loading a silicone impression material or an alginate impression material in the tray and pressing to an upper jaw within an oral cavity of a patient so as to take an impression, and a phenomenon that the set impression material cannot be retained and falls off is generated. Accordingly, this width is not preferable. If the width goes beyond 4.0 mm, a pressure is not sufficient only by loading the silicone impression material or the alginate impression material in the tray and pressing to the upper jaw within the oral cavity of the patient. Accordingly, a phenomenon that the impression material which cannot enter into the through holes 5 and is set cannot be retained and falls off is generated. Accordingly, this width is not preferable. Further, if the distance between the through hole 5 and the adjacent through hole 5 is less than twice the width of the through hole 5, the adjacent through holes 5 come too close to each other. Therefore, the impression material cannot sufficiently enter into the through holes 5 at a time of loading the silicone impression material or the alginate impression material in the tray and pressing to the upper jaw within the oral cavity of the patient so as to take the impression. Further, if the distance goes beyond fivefold, the adjacent through holes 5 are too away from each other. Therefore, there is not generated the effect that the impression material sufficiently enters into the through holes 5 so as to be retained at a time of loading the silicone impression material or the alginate impression material in the tray and pressing to the upper jaw within the oral cavity of the patient so as to take the impression. Accordingly, this distance is not preferable. It is particularly preferable that the width of the elongated through hole 5 is from 2.0 to 3.0 mm, the length of the through hole 5 is from 2 to 3 times the width, and the distance between the adjacent through holes 5 is from 3 to 18 mm.

Reference numeral 6 denotes a elongated through hole which is provided in a section corresponding to the elongated through hole 5 which is provided in the outer wall 2 at a position except a front teeth portion in the bulge portion 3 and in a section positioned at the center of the front teeth portion side at a position in the front teeth portion side in such a manner that a width reaching the bottom portion 1 is the same as a width of the elongated hole provided in the outer wall 2.

Reference numeral 7 denotes a circular through hole which is formed in the bottom portion 1 positioned at the center of the distances of the adjacent elongated through holes 5 provided in the outer wall 2 and has a diameter of 3 to 6 mm. It is necessary for the circular through hole 7 to be formed in the bottom portion 1 which is positioned at the center of the distances of the adjacent elongated through holes 5 provided in the outer wall 2 because the impression material loaded on the same position within the tray simultaneously enters into the elongated through holes 5 and 6, and the circular through holes 7 and is pushed out of the tray at a time of loading the silicone impression material or the alginate impression material in the tray and pressing to the upper jaw within the oral cavity of the patient so as to take the impression, whereby a space is generated in the set impression material, and a phenomenon that the impression material is not closely attached to the upper jaw of the patient is generated, so that there is a possibility that a good impression taking cannot be carried out. If the diameter of the circular through hole 7 is less than 3 mm, there is not generated the effect that the impression material sufficiently enters into the circular through holes 7 so as to be retained at a time of loading the silicone impression material or the alginate impression material in the tray and pressing to the upper jaw within the oral cavity of the patient so as to take the impression. Accordingly, this diameter is not preferable. If the diameter goes beyond 6 mm, the impression material enters into the circular through holes 7 too much, and the phenomenon that the impression material is not closely attached to the upper jaw of the patient is generated, so that there is a possibility that the good impression taking cannot be carried out.

Reference numeral 8 denotes an elongated end portion side through hole which is provided on a line connecting end portions in the bottom portion side of the elongated through holes 5 and 6 positioned at the closest sides to the end portions of the U-like shaped portion in the outer wall 2 and the bulge portion 3 in the end portions of the U-like shaped portion of the bottom portion 1 or a side closer to the end portion than the line and the end portion side at the center of the bulge portion 3, has a width of 1.0 to 3.0 mm and a length of 5 to 15 mm. Since the end portion side through holes 8 are provided, the impression material loaded on the closest side to the back tooth within the tray enters into each of the elongated through holes 5 and 6 which are provided in the outer wall 2 and the bulge portion 3 in the end portion of the U-like shaped portion and the end portion side through holes 8 which are provided at the center in the end portion side of the bulge portion 3, so as to be firmly retained. Accordingly, there is not generated the defect that the impression material in the end portion side (the back tooth side) of the U-like shaped portion tends to be peeled off. In the elongated end portion side through hole 8 provided for achieving the effect mentioned above, in the case that the width thereof is less than 1.0 mm, there is not generated the effect that the impression material sufficiently enters into the elongated end portion side through holes 8 so as to be retained at a time of loading the silicone impression material or the alginate impression material in the tray and pressing to the upper jaw within the oral cavity of the patient so as to take the impression taking. Therefore, this width is not preferable. Further, if the width goes beyond 3.0 mm, the impression material enters into the elongated end portion side through holes 8 too much. Accordingly, there is generated the phenomenon that the impression material in the end portion of the U-like shaped portion in the bottom portion 1 is not closely attached to the upper jaw of the patient, and there is a possibility that a good impression taking cannot be carried out.

Reference numeral 9 denotes a handle portion which is provided in the bottom surface of a center portion (the front teeth portion side) of the U-like shaped portion. The handle portion may be fixed to the bottom portion 1 or may be structured such as to be detachably provided in the bottom surface of the center portion of the U-like shaped portion in the bottom portion 1 as described in Japanese Patent Application No. 2011-217753 which was proposed by the applicant of the present patent application.

In the impression tray for an upper jaw according to the present invention mentioned above, in the case that the impression taking is carried out by loading the paste-like silicone impression material or alginate impression material on the bottom portion 1 of the U-like shaped portion between the outer wall 2 and the bulge portion 3 and pressing to the upper jaw within the oral cavity of the patient, the impression material is expanded to the outer wall 2 side and comes into contact with the undercut portion below the rim 4. Accordingly, the impression material can be prevented from floating upward and being peeled off from the tray after being set. Further, the impression material appropriately enters into the elongated through holes 5 each of which reaches the bottom portion 1 from the portion just below the rim 4 vertically to the rim 4 of the outer wall 2 and has the width of 1.5 to 4.0 mm, into the elongated through holes 6 each of which is provided in the bulge portion 3, and into the circular through holes 7 each of which is formed in the bottom portion 1 positioned at the center of the distances of the adjacent elongated through holes 5 which are provided in the outer wall 2 and has the diameter of 3 to 6 mm, and the set impression material is retained. The effect of retaining the set impression material mentioned above becomes higher in the case that the width of the elongated through holes 5 and 6 is from 2.0 to 3.0 mm and the length is from 2 to 3 times the width, and the case that the distance between the elongated through holes 5 and 6 is from 3 to 18 mm, and these cases are preferable.

Further, in the end portion of the U-like shaped portion, the impression material loaded on the closest side to the back tooth within the tray enters into the elongated end portion side through holes 8 each of which is provided on the line connecting the bottom portion side end portions of the elongated through holes 5 and 6 which are positioned in the closest side to the end portion of the U-like shaped portion in the outer wall 2 and the bulge portion 3, or in the side closer to the end portion than the line, has the width of 1.0 to 3.0 mm and the length of 5 to 15 mm, and into the elongated through holes 5 and 6 which are positioned in the closest side to the end portion of the U-like shaped portion of the outer wall 2 and the bulge portion 3 in both sides thereof, and the impression material is firmly retained. Therefore, there is not generated the defect that the impression material in the end portion side (the back tooth side) of the U-like shaped portion tends to be peeled off.

As mentioned above, in the impression tray for an upper jaw according to the present invention, in addition to the effect of the undercut portion by the rim 4 which is provided in the bottom portion 1 side along the upper end of the outer wall 2, the impression material loaded on the tray enters into the elongated through holes 5 each of which reaches the bottom portion 1 from the portion just below the rim 4 vertically to the rim 4 of the outer wall 2, is provided at the particular width and distance, into the elongated through holes 6 each of which is provided in the bulge portion 3, into the circular through holes 7 each of which is formed in the bottom portion 1 positioned at the center of the distances of the adjacent elongated through holes 5 provided in the outer wall 2 and has the particular diameter, into the elongated end portion side through holes 8 each of which is provided on the line connecting the bottom portion side end portions of the elongated through holes 5 and 6 which are positioned at the closest side to the end portions of the U-like shaped portion in the outer wall 2 and the bulge portion 3 or in the closer side to the end portion than the line, has the particular width, and into the elongated through holes 5 and 6 each of which is positioned in the closest side to the end portion of the U-like shaped portions of the outer wall 2 and the bulge portion 3 in both sides thereof, and the impression material is firmly retained. Therefore, since it is possible to prevent the set impression material from floating upward and being peeled off from the tray, it is possible to take the impression at a high precision.

What is claimed is:

1. An impression tray, comprising:
   an outer wall provided upright from an outer side of a bottom portion via a circular arc shaped portion, wherein the bottom portion comprises U shaped end portions forming a U shaped approximately flat surface with an approximately uniform width and wherein the height of the outer wall gradually decreases toward the U shaped end portions;
   a bulge portion, which bulges from an inner side of the bottom portion to form a smooth curved surface and which occludes the inner side space between the U shaped end portions;
   an inner rim provided along an inner side of an upper end of the outer wall such that an undercut portion is formed below the inner rim on the inner side of the outer wall, wherein the height of the inner rim is from 0.01 to 1 mm;
   outer elongated through holes formed in the outer wall each of which extends vertically from the bottom portion to a portion just below the inner rim except at the U shaped end portions and each of which has a width of 1.5 to 4.0 mm, wherein the distance between adjacent outer elongated through holes is from 2 to 5 times the width of the outer elongated through hole and is approximately uniform;
   inner elongated through holes formed in the bulge portion each of which extends vertically from the bottom portion and has the same width as the outer elongated through hole, wherein the inner elongated holes are provided in a section corresponding to the outer elongated through holes provided in the outer wall at a position except a front teeth portion side in the bulge portion and in a section positioned at the center of the front teeth portion side at a position in the front teeth portion side;
   circular through holes formed in the bottom portion at the center of the distances of adjacent outer elongated through holes, wherein the diameter of the circular through holes is from 3 to 6 mm; and
   elongated end portion side through holes formed in the center of the bulge portion and in the bottom portion such that the positions of the elongated end portion side through holes are closer to the U shaped end portions than a line connecting an outer elongated through hole that is nearest to the U shaped end portion on one side of the impression tray to an outer elongated through hole that is nearest to the U shaped end portion on the other side of the impression tray or are on the line, and each of the elongated end portion side through holes has a width of 1.0 to 3.0 mm and a length of 5 to 15 mm, and the directions of each of the elongated end portion side through holes are approximately parallel to each other, wherein the impression tray is made of a plastic.

2. The impression tray of claim 1, wherein the width of the inner and outer elongated through holes is from 2.0 to 3.0 mm and the length of the inner and outer elongated through holes is from 2 to 3 times the width.

3. The impression tray of claim 1, wherein the distance between adjacent outer elongated through holes is from 3 to 18 mm.

4. The impression tray of claim 1, wherein the height of the inner rim is from 1 to 0.3 mm.

5. The impression tray of claim 1, further comprising:
   an outer rim provided along an outer side of the upper end of the outer wall such that an undercut portion is formed below the outer rim on the outer side of the outer wall, wherein the height of the outer rim is from 0.01 to 1 mm.

6. The impression tray of claim 5, wherein the height of the inner rim is from 1 to 0.3 mm and the height of the outer rim is from 1 to 0.3 mm.

\* \* \* \* \*